US010087480B2

(12) United States Patent
Mayra-Makinen et al.

(10) Patent No.: US 10,087,480 B2
(45) Date of Patent: Oct. 2, 2018

(54) RAISING AND DIAGNOSING OF SEROTONIN LEVEL

(71) Applicant: Gut Guide Oy, Halikko (FI)

(72) Inventors: Annika Mayra-Makinen, Helsinki (FI); Eveliina Munukka, Turku (FI)

(73) Assignee: Gut Guide Oy (FI)

( * ) Notice: Subject to any disclaimer, the term of this patent is extended or adjusted under 35 U.S.C. 154(b) by 389 days.

(21) Appl. No.: 14/350,941

(22) PCT Filed: Oct. 12, 2012

(86) PCT No.: PCT/FI2012/050978
§ 371 (c)(1),
(2) Date: Apr. 10, 2014

(87) PCT Pub. No.: WO2013/054001
PCT Pub. Date: Apr. 18, 2013

(65) Prior Publication Data
US 2014/0301995 A1  Oct. 9, 2014

(30) Foreign Application Priority Data

Oct. 12, 2011  (FI) .................................... 20116007

(51) Int. Cl.
| | | |
|---|---|---|
| *C12Q 1/02* | (2006.01) | |
| *A61K 45/06* | (2006.01) | |
| *A61K 31/702* | (2006.01) | |
| *A61K 35/745* | (2015.01) | |
| *A61K 35/747* | (2015.01) | |
| *A61K 35/741* | (2015.01) | |
| *A23L 33/135* | (2016.01) | |

(52) U.S. Cl.
CPC .............. *C12Q 1/02* (2013.01); *A23L 33/135* (2016.08); *A61K 31/702* (2013.01); *A61K 35/741* (2013.01); *A61K 35/745* (2013.01); *A61K 35/747* (2013.01); *A61K 45/06* (2013.01); *A23V 2002/00* (2013.01); *A23V 2200/00* (2013.01); *G01N 2800/301* (2013.01); *G01N 2800/303* (2013.01); *G01N 2800/304* (2013.01); *G01N 2800/52* (2013.01)

(58) Field of Classification Search
None
See application file for complete search history.

(56) References Cited

U.S. PATENT DOCUMENTS

2011/0152309 A1  6/2011  Beppu et al.

FOREIGN PATENT DOCUMENTS

| | | | |
|---|---|---|---|
| EP | 0753303 | A2 | 1/1997 |
| EP | 1974734 | A1 | 10/2008 |
| WO | 2004/015421 | A1 | 2/2004 |
| WO | 2004/098622 | A2 | 11/2004 |
| WO | 2011/058535 | A1 | 5/2011 |
| WO | 2011/060123 | A1 | 5/2011 |
| WO | 2011/108826 | A2 | 9/2011 |

OTHER PUBLICATIONS

Desbonnet et al. "Effects of the Probiotic Bifidobacterium Infantis in the Maternal Separation Model of Depression" Neuroscience 170 (2010) 1179-1188.*
Meidical Dictionary "Microbiota" accessed on Dec. 15, 2016, 2 pgs.*
Search Report issued in corresponding Finnish Patent Application No. 20116007, dated Jun. 28, 2012.
Backhed, Fredrik et al. Host-Bacterial Mutualism in the Human Intestine. Science, vol. 307 1915-1920 (2005).
Desbonnet, Lieve et al. The probiotic Bifidobacteria infantis: An assessment of potential antidepressant properties in the rat. Journal of Psychiatric Research 43:164-174, (2009).
Franks, Alison H. et al. Variations of Bacterial Population in Human Feces Measured by Fluorescent In Situs Hybridization with Group-Specific 16S rRNA-Targeted Oligonucleotide Probes. Applied and Environmental Microbiology, vol. 64, No. 9, p. 3336-3345, (1998).
Hooper, Lora V. et al. Comnensal Host-Bacterial Relationships in the Gut. Science 292, 1115 (2001).
Jimenez, M. Bixquert. Treatment of irritable bowel syndrome with probiotics. An etiopathogenic approach at last? Rev Esp Enferm Dig (Madrid) vol. 101 No. 8, pp. 553-564, (2009).
Rao, A. Venket et al. A randomized, double-blind, placebo-controlled pilot study of a probiotic in emotional symptoms of chronic fatigue syndrome. Gut Pathogens, pp. 1-6 (2009).
Vaahtovuo, Jussi et al. Quantification of bacteria in human feces using 16S rRna-hybridization, DNA-staining and flow cytometry. Journal of Microbiological Methods 63: 276-286, (2005).
Chien, Yi-wen, et a. "Lactobacillus fermentum PCC (ProBio Pc) improves intestinal bacteria flora", Fed. of American Society for Experimental Biology, vol. 19, No. 4, 281.1, Suppl, Mar. 1, 2005, p. A448.

(Continued)

*Primary Examiner* — Thane Underdahl
(74) *Attorney, Agent, or Firm* — Banner & Witcoff, Ltd.

(57) ABSTRACT

The invention is based on a correlation observed between serotonin level and intestinal flora. The invention relates to a relative proportion of bifidobacteria in the intestine and in particular to a product increasing the ratio of bifidobacteria to Clostridia, to be used for raising the serotonin level. The invention also relates to a method for estimating a health risk associated with serotonin depletion by determining a relative proportion between bifidobacteria or Clostridia in the intestine or their ratio to one another. The invention further relates to a method for selecting a form of therapy for raising the serotonin level by determining a relative proportion between bifidobacteria or Clostridia in the intestine or their ratio to one another.

4 Claims, No Drawings

(56) References Cited

OTHER PUBLICATIONS

Sepp, E., et al. "Intestinal microbiota and immunoglobulin E responses in 5-year-old Estonian children," Clinical & Experimental Allergy, vol. 35, No. 9, Sep. 1, 2005, pp. 1141-1146.

De Palma, Giada et al., "Intestinal dysbiosis and reduced immunoglobulin-coated bacteria associated with coeliac disease in children", BMC Microbiology, Biomed Central Ltd, GB, vol. 10, No. 1, Feb. 24, 2010, p. 63.

Ogata, T et al., "Effect of Bifidobacterium Longum BB536 Yoghurt Administration on the Intestinal Environment of Healthy Adults", Microbial Ecology in Health & Disease,, vol. 11, No. 1, Mar. 1, 1999, pp. 41-46.

* cited by examiner

RAISING AND DIAGNOSING OF SEROTONIN LEVEL

RELATED APPLICATION DATA

This application is a National Stage Application under 35 U.S.C. 371 of co-pending PCT application PCT/FI2012/050978 designating the United States and filed Oct. 12, 2012; which claims the benefit of FI application number 20116007 and filed Oct. 12, 2011 each of which are hereby incorporated by reference in their entireties.

FIELD OF THE INVENTION

The present invention relates to serotonin depletion and to a health risk associated therewith. More particularly, the invention relates to a product to be used for raising the serotonin level. The invention further relates to a method for estimating a health risk associated with serotonin depletion and to a method for selecting a form of therapy for raising the serotonin level.

BACKGROUND OF THE INVENTION

Serotonin, i.e. 5-hydroxytryptamine (5-HT), is a tissue hormone released from thrombocytes and constricting blood vessels, and also a neurotransmitter in the brain. Serotonin depletion may manifest itself as melancholy, apathy, depression, insomnia, change of appetite and chronic fatigue. In addition to its central nervous system activity, serotonin regulates bowel motility and sensing of pain. Serotonin depletion in the body has also been substantially associated with different disturbances in the intestines, such as IBS (irritable bowel syndrome) and "leaky gut".

A low serotonin level thus presents a health risk. Serotonin depletion can be treated by various drugs, such as selective serotonin reuptake inhibitors (SSRI drugs) or monoamine oxidase inhibitors (MAO inhibitors). Like drugs in general, also those raising the serotonin level may have more or less harmful side effects.

The present invention now offers an alternative for raising the serotonin level. The invention also provides means for determining a health risk associated with a low serotonin level, for reducing the risk and for selecting the right form of therapy. The invention makes use of the gut microbiota of the target.

The composition of gut microbiota has been demonstrated to have numerous effects on the wellbeing and health of the host (Hooper L. V., Gordon J. *Science* 2001; 292:1115-8; and Bäckhed, F et al. 2005. *Science* 307, 1915-1920). Use probiotic bacteria has been suggested for promoting development of early bifidogenic gut microbiota in order to reduce the risk of overweight or obesity in small children later in life (EP 1 974 734). Rats have been fed with bifidobacteria, and the rats that received bifidobacteria were found to have more tryptophan and kynurenic acid in plasma and less inflammation factors (IFN-γ, TNF-α and IL-6) than the control animals. Tryptophan is a precursor of serotonin (Desbonnet L et al. *J Psychiatr Res.* 2008; 43:164-174). The authors speculate that bifidobacteria may have anti-depressant effects. They emphasize, however, that the results are preliminary and must be interpreted with caution. Although bifidobacteria raised peripheral tryptophan level, they did not raise the serotonin level in the central nervous system. Neither did bifidobacteria have any effect on the behaviour of rats in a forced swim test, which is for testing antidepressants. Further, it is to be kept in mind that results obtained in animal testing are not directly applicable to humans. Another point worth mentioning is that leptin acts differently in rats than in humans. It is also to be remembered that so far the understanding of the functioning of the brain-gut connection and gut microbes possibly regulating it is fairly inadequate. The present invention enhances this understanding.

BRIEF DESCRIPTION OF THE INVENTION

As far as is known, the present invention is based on the first study made on human material, in which it was surprisingly discovered that certain groups of bacteria belonging to the normal flora in the intestine, bifidobacteria and non-pathogenic clostridia, associate with the serotonin concentration in serum. By modifying the relative proportions of these bacteria in the intestine, it is possible to raise the serotonin level and thereby reduce the health risks associated with serotonin depletion, or to treat or prevent diseases associated with a low serotonin level. Moreover, examination of intestinal flora helps in selecting the right form of therapy for raising the serotonin level.

The invention relates to a product increasing the relative proportion of bifidobacteria in the intestine to be used for raising the serotonin level in a target. The invention also relates to a product increasing the ratio of bifidobacteria to clostridia in the intestine to be used for raising the serotonin level in a target.

The invention further relates to a method for estimating a health risk associated with serotonin depletion, in which method a relative proportion of bifidobacteria in the intestine is determined in vitro, the relative proportion of the bifidobacteria correlating negatively with a health risk. The invention further relates to a method for estimating a health risk associated with serotonin depletion, in which method a ratio of bifidobacteria to clostridia in the intestine is determined in vitro, the ratio of the bifidobacteria to the clostridia correlating negatively with a health risk. The invention further relates to a method for estimating a health risk associated with serotonin depletion, in which method a relative proportion of clostridia in the intestine is determined in vitro, the relative proportion of the clostridia correlating negatively with a health risk.

The invention further relates to a method for selecting a form of therapy for raising the serotonin level in a target, in which method a relative proportion of bifidobacteria in the intestine is determined in vitro, the relative proportion of the bifidobacteria correlating negatively with selecting a form of therapy in which the target is administered a product raising the relative proportion of bifidobacteria. The invention further relates to a method for selecting a form of therapy for raising the serotonin level in a target, in which method the ratio of bifidobacteria to clostridia in the intestine is determined in vitro, the ratio of the bifidobacteria to the clostridia correlating negatively with selecting a form of therapy in which the target is administered a product raising the relative proportion of the bifidobacteria. The invention further relates to a method for selecting a form of therapy for raising the serotonin level in a target, in which method a relative proportion of clostridia in the intestine is determined in vitro, the relative proportion of the clostridia correlating positively with selecting a form of therapy in which the target is administered a product raising the relative proportion of clostridia.

Further still, a method for raising the serotonin level in a target is described, in which method the target in need of this kind of treatment is administered a potent amount of a product increasing the relative proportion of bifidobacteria in the intestine.

One of the advantages of the product used in accordance with the invention is that it is natural, safe and inexpensive. Moreover, it does not have harmful side effects, such as an increasing effect on body weight.

Preferred embodiments of the invention are disclosed in the dependent claims.

DETAILED DESCRIPTION OF THE INVENTION

"The relative proportion of bifidobacteria" refers to the proportion of bifidobacteria in relation to other bacteria in the intestine, normally to the total bacteria and particularly to clostridia. The product of the invention to be used for raising the serotonin level is capable of increasing the relative proportion of bifidobacteria in the total bacteria. In particular, it is capable of increasing the ratio of bifidobacteria to clostridia in the intestine. It may also have a decreasing effect on the relative proportion of clostridia in the total bacteria of the intestine.

The product increasing the relative proportion of bifidobacteria in the intestine may be selected from a group consisting of bifidobacteria, prebiotics, bifidobacteria+prebiotics, a product stimulating bifidobacteria and any combination of these. The bifidobacteria are preferably selected from strains used as probiotics, such as *Bifidobacterium longum, Bifidobacterium bifidum, Bifidobacterium breve* and *Bifidobacterium. infantis*, and e.g. *Bifidobacterium, animalis* subsp. *lactis* Bb-12 and *Bifidobacterium lactis* B1. "A probiotic" refers to a microbe or a component thereof that has a positive effect on the health of the host. Usually it is a live microbe. "A prebiotic" is a component that is usually a carbohydrate (an oligo- or polysaccharide) and has a selective promoting effect on the growth or activity of one or more bacterial strains in the colon. A prebiotic is preferably a fructo- or galacto-oligosaccharide, fibre, cereal fibre in particular, such as b-glucan of oat, polydextrose, special sugar, such as isomaltulose, or a fatty acid, such as omega-3 fatty acid, or any mixture of these. The product increasing the relative proportion of bifidobacteria preferably contains both bifidobacteria and prebiotics. The product stimulating bifidobacteria may be a product containing propionic acid bacteria, such as *Propionibacterium freudenreichii, Propionibacterium shermanii*, and/or lactobacilli, such as *Lactobacillus acidophilus, Lactobacillus rhamnosus, Lactobacillus casei* or *Lactobacillus lactis*.

According to an embodiment, the product of the invention is one that increases the ratio of bifidobacteria to clostridia in the intestine, such as lactic acid bacteria which have been shown to inhibit the growth of clostridia, such as lactobacilli, e.g. certain strains of *Lactobacillus rhamnosus* and *Lactobacillus casei*.

The above-described bacteria and/or prebiotics and/or other active substances acting on the gut flora may be administered mixed in food or drink, for example, or separately in the form of a capsule, granulate, powder or liquid, for example. In other words, the product described here may be in the form of a food, drink, capsule, granulate, powder or liquid containing substances acting on the gut flora. "A potent amount" of a product acting on the gut flora refers to an amount sufficient for changing the relative proportion of bifidobacteria or clostridia in the intestine and, in particular, the ratio of bifidobacteria to clostridia.

The product described above may be used for treating serotonin depletion, i.e. for raising the serotonin level in the body. The body's serotonin level can be conveniently determined from serum. "Serotonin depletion" refers to a serotonin level that is lower than the average level in normal population, with standard deviations included, i.e. usually less than 350 nmol/L in the serum. Low 5-hydroxytryptamine concentrations may be found in depression. By administering the product that raises the serotonin level it is possible to treat diseases associated with serotonin depletion. A low serotonin level in the brain has been demonstrated to be have a causal connection e.g. to depression, insomnia and appetite. Depressed people may often medicate themselves by eating, in which case a low serotonin level may also lead to obesity. The present study surprisingly revealed that the serotonin level of the serum correlates negatively with visceral body fat. Visceral fat is a fat tissue covering the internal organs in the peritoneal cavity and correlates strongly with many serious diseases, such as metabolic syndrome, type 2 diabetes or hypertension. Subcutaneous fat tissue, on the other hand, has been suggested to have even a protective effect. The product increasing the relative proportion of bifidobacteria may be used advantageously for example in the treatment or prevention of mental disorders and depression and for preventing the formation of visceral fat or for reducing the amount thereof.

The present invention opens up interesting views on product applications modifying the microbiota to support anti-depression and anti-obesity. A person may be provided with a product designed individually for him/her to modify the normal gut flora on the basis of the serotonin concentration of his/her serum.

A health risk associated with serotonin depletion may be estimated by determining the relative proportion of bifidobacteria and/or clostridia or their ratio to one another in the intestine. If the relative proportion of bifidobacteria and, in particular, if the ratio of bifidobacteria to clostridia is small, the risk to health is high. Correspondingly, if the relative proportion of clostridia is high, the risk to health is high as well. The health risk concerns particularly the risk to come down with the above-mentioned diseases associated with serotonin depletion.

A suitable form of treatment for raising the serotonin level may be selected by analysing the relative proportion of bifidobacteria and/or clostridia or their ratio to one another in the intestine. If the relative proportion of bifidobacteria is small or the relative proportion of clostridia is high, the product increasing the relative proportion of bifidobacteria is selected for raising the serotonin level. The same applies especially if the ratio of bifidobacteria to clostridia is low. Said form of treatment is particularly suitable for treating or preventing diseases associated with serotonin depletion.

The health risk associated with serotonin depletion may be estimated and a suitable form of treatment may be selected by analysing the microbiota in the gut of the body. More specifically, the relative proportion of bifidobacteria or clostridia in the intestine can be determined from the total bacteria in the intestine and, in particular, the ratio of bifidobacteria to clostridia is determined. This ratio is here referred to as the "MOODindex" and it is obtained by dividing the relative proportion of bifidobacteria by the relative proportion of clostridia. The MOODindex produces the best correlations. The MOOD index is particularly obtained by dividing the percentage of bifidobacteria useful for gut health by the percentage of clostridia group XIVa that belongs to the normal gut flora.

The expression "correlates negatively" means that when one variable increases, another one decreases, while "correlates positively" means that when one variable increases, another one increases as well, and vice versa. Consequently, the higher a person's relative proportion of bifidobacteria or MOODindex is, the smaller is his/her risk of getting a disease associated with serotonin depletion (negative correlation) and, correspondingly, the higher the relative proportion of clostridia a person has, the bigger is his/her risk of getting a disease associated with obesity (positive correlation). Further, the lower a person's relative proportion of bifidobacteria or MOODindex is, the more there is reason to select a form of treatment in which the person is administered the product increasing the relative proportion of bifidobacteria in the intestine (negative correlation). Correspondingly, the higher the relative proportion of clostridia is, the greater is the reason for selecting the treatment in question (positive correlation). Normally, the aim is to obtain a MOODindex value of at least one. If the MOODindex is less than 1, a personalized probiotic and or prebiotic composition is used in an attempt to raise it to a level exceeding 1. If the MOODindex is higher than 1, a personalized probiotic and or prebiotic composition is used in an attempt to maintain the index level.

Normally a fecal sample of the target is examined to quantitatively determine bifidobacteria, clostridia and/or total bacteria by methods known per se. Bifidobacteria and clostridia are well known, taxonomically identifiable bacteria groups. "Bifidobacteria" are gram-positive, immobile anaerobic bacteria that appear in the digestive tract (and belong to the *Bifidobacteriaceae* family and particularly to the *Bifidobacterium* genus). "Clostridia" are spore-forming, gram-positive anaerobic bacteria (belonging to the Clostridia class) and which include *Clostridium* and *Eubacterium* genera, for example. In the context of the invention, clostridia are particularly non-pathogenic clostridia of clostridia group XIVa belonging to the normal gut flora. The proportion of bifidobacteria and/or clostridia in the total bacteria and/or the ratio of bifidobacteria to clostridia is preferably determined by a method based on 16S rRNA hybridisation, DNA staining and a method based on flow cytometry (FCM-FISH), which allows different intestinal bacteria groups to be determined rapidly and reliably.

"A target" in this context refers to an animal, particularly a mammal, including man. Preferably the target is a person.

Example 1

Fecal samples were collected from 57 healthy adult Finns (19 men, 38 women). The samples were stored frozen and the bacteria were isolated from them using the method described above (Vaahtovuo J et al. *J Microbiol Methods.* 2005; 63:276-286). The bacteria were fixed and the total bacteria amounts (number per gram of dry matter of feces) were determined from the samples, and also, the following six bacteria groups or genera significant to health and wellbeing were determined from them: bifidobacteria, *Bacteroides*, enteric group, *Atopobium, Faecalibacterium prausnitzii* and *Clostridium* XIVa, which means a cluster of clostridia XIVa, i.e. also known as the Erec group (Franks et al. 1998, *Appl. Environ. Microbiol.* 64: 3336-3345). All of the above bacteria groups belong, in the light of present knowledge, to what is called a normal human microbiota. The determination was made using a patented method based on 16 S rRNA hybridisation, DNA staining and flow cytometry (FCM-FISH) (Vaahtovuo J et al. 2005 supra and WO2004/015421). In addition, the dry matter percentage of the samples was determined.

A fasting sample blood test was taken from the targets of the study to determine numerous biomarkers associated with sugar and lipid metabolism, inflammation factors and hormones, including serotonin.

The body composition of the targets of study was determined by a method based on bioimpedance, and visceral fat by magnetic resonance imaging (MRI) in which the surface area of visceral fat in the abdominal area is calculated from an image by computer tomography. The test persons filled in questionnaires on their way of life, medical history and medications, if any, and on physical activity. They also kept a food diary for three days. Fecal samples of two test persons had to be discarded from the material due to a chronic gut disease. One of the test persons had an exceptionally low serotonin level due to SSRI medication, and this value was discarded from the analyses.

After the bacteria analyses, the so-called MOODindex was calculated for each fecal sample by dividing the percentage of bifidobacteria useful for gut health by the percentage of clostridia group XIV that belongs to the normal gut flora. Correlations between the different variables were determined by using Pearson's correlation coefficient.

RESULTS

Table 1 shows the basic data determined on the test persons in the study. In table 1 the test persons are grouped according to gender. Men were older and naturally also heavier than women. In contrast, the women had a higher fat percentage than the men.

TABLE 1

Basic data on the test persons (average, SD in parentheses)

|  | Men | Women | T test |
|---|---|---|---|
| Age | 52 (4) | 36 (6) | ***, p = 0.001 |
| Weight (kg) | 84 (12) | 69 (13) | ***, p < 0.001 |
| Waist circumference (cm) | 97 (10) | 84 (13) | ***, p < 0.001 |
| BMI (kg/m$^2$) | 27.1 (4.1) | 24.7 (4.6) | p = 0.066 |
| Fat percentage | 28 (7) | 36 (10) | ***, p = 0.002 |
| Blood pressure (mmHg) | 135/80 (12/9) | 127/77 (16/10) | p = 0.051/0.208 |

Table 2 shows the average values for dry matter content in the feces and for the relative proportions of the different bacteria groups determined by FCM-FISH.

TABLE 2

Analyses of fecal samples (average, SD in parentheses)

|  | Men | Women | T test |
|---|---|---|---|
| Dry matter in feces (%) | 24 (7) | 27 (8) | p = 0.189 |
| Bifidobacteria (%) | 4.4 (2.9) | 5.6 (5.3) | p = 0.915 |
| Bacteroides (%) | 3.6 (2.6) | 2.9 (1.2) | p = 0.352 |
| Enteric group (%) | 0.4 (0.2) | 0.8 (1.3) | ***, p = 0.007 |
| Atopobium (%) | 3.7 (2.3) | 3.5 (1.7) | p = 0.826 |
| F. prausnitzii (%) | 10.1 (4.8) | 6.9 (4.1) | *, p = 0.012 |
| Clostridium XIVa | 12.4 (8.7) | 8.5 (7.7) | p = 0.054 |

Intestinal Microbiota vs. Serotonin

The sample material was divided into tertiles according to the serotonin concentration.

Group I (low serotonin concentr. <33.3%)
Group II (serotonin concentr. >33.3% and <66.6%)
Group III (high serotonin concentr. >66.6%)

The groups of different serotonin levels differ from one another on all the parameters examined. Table 3 shows the statistical difference between the different serotonin level groups regarding the total amount (number/g) of intestinal bacteria and the percentage proportions of bifidobacteria and clostridia XIVa in the different groups.

TABLE 3

Average values for the total amount (number/g) of intestinal bacteria and the percentage proportions of the different groups in the different serotonin level groups.

|  | Group I | Group II | Group III | P# |
|---|---|---|---|---|
| Serotonin (nmol/l) | 129 | 206 | 318 | <0.001 |
| Total bacteria | $2.0 \cdot 10^{11}$ | $2.6 \cdot 10^{11}$ | $2.9 \cdot 10^{11}$ | 0.029 |
| Bifidos (%) | 3.3 | 4.3 | 7.1 | 0.029 |
| *Clostridium* XIVa (%) | 15.4 | 7.0 | 7.0 | 0.001 |
| MOODindex* | 0.32 | 0.9 | 1.7 | <0.001 |

*MOODindex calculated for each person by dividing the bifidobacteria (%) by clostridia XIV (%). The average MOODindex in the groups represents the average of the indexes of all persons in the group concerned.
Calculated using analysis of variance (or ANOVA). The result shows whether there is a statistically significant difference between the average values for the three groups.

As regards the entire study material, the connection between serotonin and different intestinal bacteria was calculated using Pearson's correlation coefficient. The study showed a significant, positive correlation (r=0.372, p=0.014) between the total bacteria amount and the serotonin concentration in the serum. In this study, a significant, positive correlation (r=0.437, p=0.001) was observed between bifidobacteria (% of all bacteria) and the serotonin concentration in the serum. However, a negative correlation (r=0.489, p<0.001) was observed between clostridia XIVa (%) and the serotonin concentration. The MOODindex showed a statistically significant and positive correlation, and a more intensive one than individual groups of bacteria, with the serotonin concentration (r=0.587, p<0.001). The results are collected in table 4.

TABLE 4

Correlations, the entire material

|  | Total bacteria (number/g average) | Bifidos (%) Percentage proportion (%) of all bacteria in the sample | *Clostridium* XIVa (Percentage proportion (%) of all bacteria in the sample) | MOODindex |
|---|---|---|---|---|
| Serotonin | small, pos. r p = 0.014* | mod. pos. r, p = 0.001** | mod. neg. r, p < 0.001** | mod. pos. r, p < 0.001** |

Age and gender may have a bearing on the serotonin concentration in the serum. Statistical analyses were also carried out on a material consisting only of women (n=38, Table 5). The above-indicated correlations between serotonin in the serum and the total bacteria and the percentage proportions (%) of bifidobacteria were significant also in this smaller material (r=0.403, p=0.033 and r=0.522, p=0.001).

A significant, positive correlation (r=0.663, p<0.001) was observed between serotonin and MOODindex calculated from the samples.

When age, was taken into account in the analysis of the material consisting only of women, a significant negative correlation continued between the serotonin in the serum and *clostridium* XIVa (p=0.008) and a positive correlation between serotonin and the MOODindex (p=0.003). Between serotonin and the bifidobacteria the positive correlation was almost statistically significant (p=0.065), but there is a clear trend to be seen between two variables.

TABLE 5

Correlations, women

|  | Total bacteria (number/g average) | Bifidos (%) (Percentage proportion (%) of all bacteria in the sample) | *Clostridium* XIVa (Percentage proportion (%) of all bacteria in the sample) | MOODindex |
|---|---|---|---|---|
| Serotonin | small, pos. r p = 0.033* | mod. pos. r, p = 0.001** | mod. neg. r, p < 0.001** | strong pos. r, p < 0.001** |

Visceral Fat

The serotonin concentration in the serum correlated significantly and negatively with visceral fat (p=0.003). In addition, visceral fat correlated positively with the relative proportion of *clostridium* group XIVa (p=0.002), while a clear negative trend was observed in the correlation with the relative proportion of bifidobacteria (p=0.098). Between the MOODindex and visceral fat the correlation is negative (p=0.002). The results are shown in Table 6.

In the material consisting only of women, visceral fat correlated negatively with serotonin (p=0.045) and with MOODindex (p=0.011) and almost significantly with bifidobacteria (p=0.066). A positive, significant correlation was observed between *clostridium* group XIVa and visceral fat (p=0.033). The results are shown in Table 7.

TABLE 6

Correlations, the entire material

|  | Bifidobacteria (%) | *Clostridium* XIVa (%) | MOODindex |
|---|---|---|---|
| Visceral Fat (%) | neg. r, p = 0.098 | mod. pos. r, p = 0.002** | mod. neg. r, p = 0.002** |

TABLE 7

Correlations, women

|  | Bifidobacteria (%) | *Clostridium* XIVa (%) | MOODindex |
|---|---|---|---|
| Visceral Fat (%) | mod. neg. p = 0.066* | mod. pos. r, p = 0.033* | mod. neg. r, p = 0.011* |

Example 2

Five Finns participate in an intervention where the composition of their gut microbiota and MOOD index are analysed before and after a probiotic (Cell Biotech) and/or prebiotic (glucomannan) intervention.

The study employs a probiotic powder containing a total of 10e9 cfu/day. The probiotic powder consists of strains

*Lactobacillicus rhamnosus* GG, *Lactobacillicus rhamnosus* LRH 19, *Lactobacillicus planatarum* BGP12 and *Bifidobacterium lactis*. 0.7 g/day of xylo-oligosaccharides are used as prebiotics.

During the test, the test persons consume one bag (1 g) of probiotic powder a day, mixed in yoghurt, sour whole milk (viili), quark or cold liquid, for example. The dose of glucomannan was 3 g a day (3×1 g) as capsules.

It will be apparent to a person skilled in the art that as technology advances, the basic idea of the invention may be implemented in many different ways. The invention and its embodiments are thus not restricted to the examples described above but may vary within the scope of the claims.

The invention claimed is:

1. A method for estimating a human target's health risk associated with serotonin depletion, comprising determining the percentage of bifidobacteria and clostridia in total fecal microbiota of a fecal sample obtained from the target using 16sRNA hybridization, DNA staining, and/or flow cytometry, and calculating a ratio of said bifidobacteria to said clostridia in the sample, wherein the calculated ratio higher than 1 indicates that the target's health risk is not increased.

2. A method for estimating a human target's health risk associated with serotonin depletion, comprising determining the percentage of bifidobacteria and clostridia in total fecal microbiota of a fecal sample obtained from the target using 16sRNA hybridization, DNA staining, and/or flow cytometry, and calculating a ratio of said bifidobacteria to said clostridia in the sample, wherein the calculated ratio of less than 1 indicates that the target's health risk is increased.

3. A method for selecting a form of therapy for raising the serotonin level in a human target, comprising determining the percentage of bifidobacteria and clostridia in total fecal microbiota of a fecal sample obtained from the target using 16sRNA hybridization, DNA staining, and/or flow cytometry, and calculating a ratio of said bifidobacteria to said clostridia in the sample, wherein the calculated ratio of less than 1 indicates that the form of therapy to be selected for raising the serotonin level in the target comprises administering to the target a product which increases the relative proportion of bifidobacteria to clostridia in the intestine of the target.

4. A method for raising serotonin level in a human target, in which method the target in need of this kind of treatment has a ratio of bifidobacteria to clostridia of less than 1 in a fecal sample obtained from the target using 16sRNA hybridization, DNA staining, and/or flow cytometry, and the method comprises administering a potent amount of a product which increases the relative proportion of bifidobacteria to clostridia in the intestine of the target for raising the serotonin level in the target.

* * * * *